US011587678B2

(12) United States Patent
Goetz et al.

(10) Patent No.: US 11,587,678 B2
(45) Date of Patent: Feb. 21, 2023

(54) MACHINE LEARNING MODELS FOR DIAGNOSIS SUSPECTING

(71) Applicant: Clover Health, Jersey City, NJ (US)

(72) Inventors: Melanie Goetz, Oakland, CA (US); Christopher James Lauinger, Golden, CO (US)

(73) Assignee: Clover Health, Jersey City, NJ (US)

( * ) Notice: Subject to any disclaimer, the term of this patent is extended or adjusted under 35 U.S.C. 154(b) by 402 days.

(21) Appl. No.: 16/827,505

(22) Filed: Mar. 23, 2020

(65) Prior Publication Data

US 2021/0295996 A1 Sep. 23, 2021

(51) Int. Cl.
*G06F 17/18* (2006.01)
*G16H 50/20* (2018.01)
*G16H 50/30* (2018.01)
*G06F 9/54* (2006.01)
*G06N 20/00* (2019.01)
*G16H 10/60* (2018.01)

(52) U.S. Cl.
CPC ............ *G16H 50/20* (2018.01); *G06F 9/542* (2013.01); *G06F 17/18* (2013.01); *G06N 20/00* (2019.01); *G16H 10/60* (2018.01); *G16H 50/30* (2018.01)

(58) Field of Classification Search
CPC ........ G16H 50/20; G16H 10/60; G16H 50/30; G06N 20/00
See application file for complete search history.

(56) References Cited

U.S. PATENT DOCUMENTS

| | | | | |
|---|---|---|---|---|
| 2015/0278457 | A1* | 10/2015 | De la Torre | G16H 50/20 |
| | | | | 705/3 |
| 2016/0328434 | A1* | 11/2016 | Barbas | G06F 16/21 |
| 2019/0392579 | A1* | 12/2019 | Savadjiev | G16H 30/40 |
| 2020/0232046 | A1* | 7/2020 | Kennedy | C12Q 1/6806 |
| 2020/0320682 | A1* | 10/2020 | Alexander | G06V 10/507 |
| 2021/0233662 | A1* | 7/2021 | Sun | G06F 17/18 |
| 2021/0295996 | A1* | 9/2021 | Goetz | G06N 20/00 |
| 2021/0383921 | A1* | 12/2021 | Isobe | G16H 50/20 |

* cited by examiner

*Primary Examiner* — David E Choi
(74) *Attorney, Agent, or Firm* — Lee & Hayes, P.C.

(57) ABSTRACT

The present disclosure describes methods and systems for machine learning models utilized for diagnosis suspecting. These methods and systems utilize machine learning models may be trained to diagnose diseases or conditions. The models may be trained with data from disparate sources that are aggregated and formatted to be utilized in these models.

20 Claims, 7 Drawing Sheets

GENERATE MACHINE LEARNING MODELS CONFIGURED TO DIAGNOSE DISEASE(S) OR CONDITION(S) FOR MEDICAL PATIENT 702

↓

RECEIVE DATA FROM MULTIPLE DISPARATE SOURCES VIA COMPUTING NETWORK 704

↓

FORMAT DATA INTO MODEL FEATURES CONFIGURED TO BE INPUT INTO MACHINE LEARNING MODELS 706

↓

INPUT MODEL FEATURES INTO MACHINE LEARNING MODELS 708

↓

GENERATE UTILIZING AT LEAST MACHINE LEARNING MODELS, OUTPUT DATA INDICATING POTENTIAL DIAGNOSIS FOR DISEASE(S) OR CONDITION(S) FOR MEDICAL PATIENT 710

↓

RECEIVE, FROM A COMPUTING DEVICE EXECUTING AN APPLICATION, INDICATION THAT MEDICAL PATIENT WILL BE SEEN BY PHYSICIAN AT GIVEN TIME 712

↓

SEND, TO THE COMPUTING DEVICE AND AT GIVEN TIME, NOTIFICATION INCLUDING THE POTENTIAL DIAGNOSIS 714

MACHINE LEARNING MODELS FOR DIAGNOSIS SUSPECTING

BACKGROUND

Determining a diagnosis for an undiagnosed disease or condition in a medical patient may be desired. Described herein are improvements in technology and solutions to technical problems that can be used to, among other things, assist in determining diagnoses.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 7 illustrates a flow diagram of another example process for utilizing machine learning models for diagnosis suspecting.

DETAILED DESCRIPTION

Figure 1:
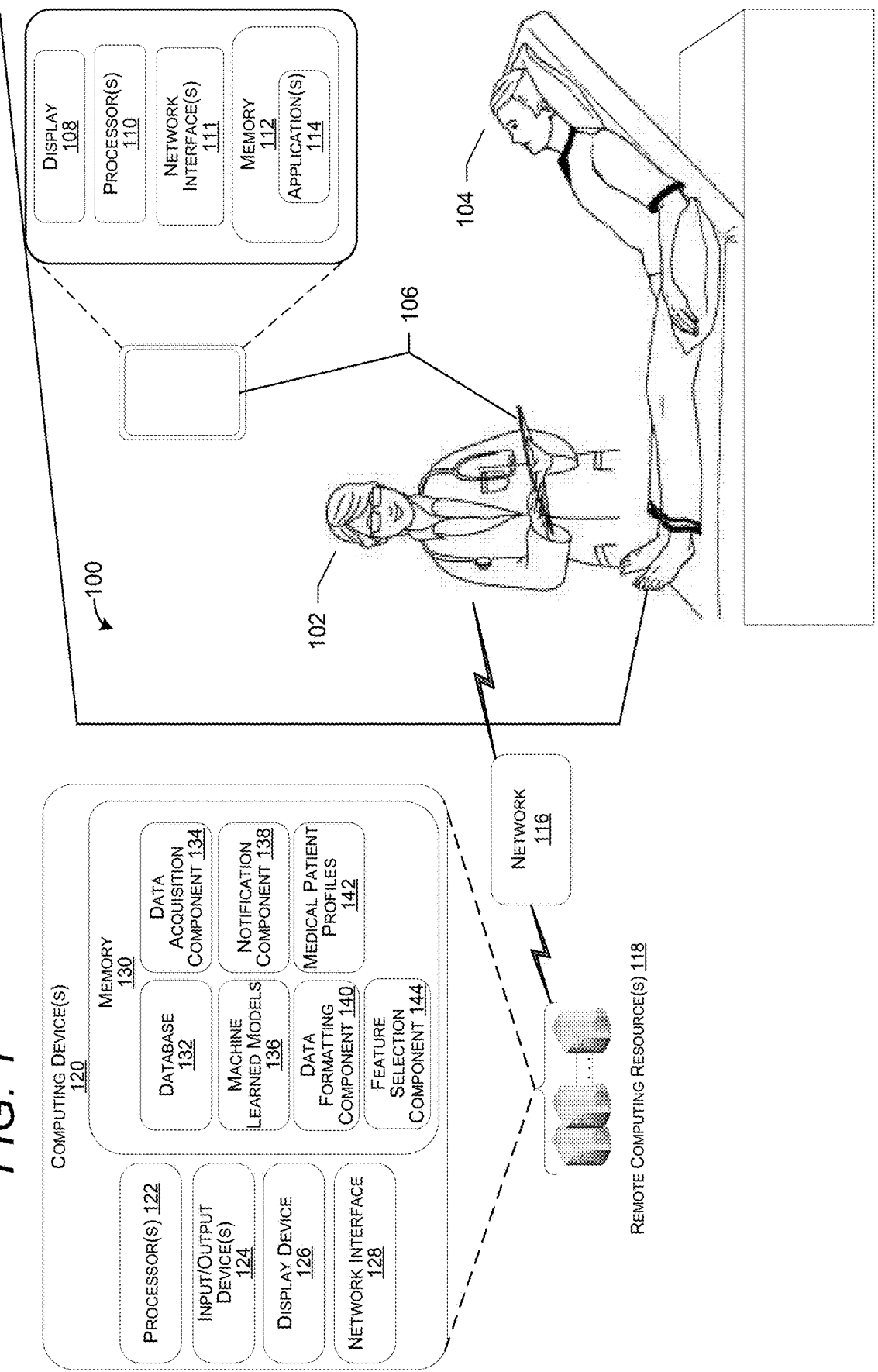
FIG. 1 illustrates a schematic diagram of an example environment for the utilization and implementation of diagnosis suspecting architectures and systems.

Systems and methods for utilizing machine learning models for diagnosis suspecting are described herein. Accurate diagnosing relies on data to drive probabilities for decision making. This process can be optimized and improved through the use of large, complex data sets and machine learning to recognize patterns and provide accurate probabilities of diagnosis. For example, data from disparate sources that may not traditionally be viewed or viewable together for diagnostic purposes (e.g. laboratory data, medical record data, geographical data) can be combined into larger data sets, which can then utilize machine learning models and data analytic pipelines to diagnose diseases that may otherwise go undetected. These diagnoses may then be confirmed, or rejected, by a medical service provider (e.g. physician, nurse practitioner, physician's assist). In examples, these diagnoses may be surfaced and then presented to a medical service provider (e.g. physician, nurse practitioner, registered dietitian, physician's assistant), wherein a given diagnosis may be either confirmed or rejected. In these and other examples, the confirmation or rejection of the diagnosis may then be used to update the data and machine learning models to improve diagnosis accuracy for future diagnosis suspecting and surfacing.

The present innovation is directed to systems and methods that generate machine learning models configured to diagnose one or more diseases or conditions and utilize the trained machine learning models to determine a likelihood that a disease or condition should be diagnosed in a medical patient and then surfacing that diagnoses to a medical service provider. By way of example, machine learning models may be trained on a large data set, wherein individual machine learning models are trained to determine a likelihood that a disease or condition should be diagnosed in a medical patient.

The data used to train the machine learning models may be received into a database from multiple disparate data sources via a computing network. On their own, the data from the disparate sources are likely to exist in disparate formats and may be formatted into coherent data structures and formats, particularly formats associated with the machine learning models. These data structures may be multi-dimensional data and may include associated metadata that may be unpacked and formatted within the data structures. Annotations may be included in the disparate data sources and may be formatted. The data structures are further formatted into model features that are configured to be input into machine learning models. Formatting data into model features may include several data manipulations. For example, data may be standardized or normalized to bring data with different scales into a similar scale. New data may be generated in appropriate scales using other techniques appropriate for machine learning models.

Data standardization is the process of rescaling the features so that they will have the properties of a Gaussian distribution where the mean is equal to zero and the standard deviation is equal to one. Data normalization is the process of rescaling the features such that the range of the data is fixed. For example, the range can be fixed between zero and one, and normalized based on a sigmoid function. In other examples, the range can be fixed between zero and 10, and normalized based on a rectified linear unit function. While these standardization and normalization approaches are discussed, other approaches may be utilized.

Formatted data and model features may be input into machine learning models. The machine learning models may be individually trained to specific diagnoses. The machine learning models receive the inputted, formatted data and produce output data. The output data includes a probability and/or confidence value that a medical patient may be diagnosed with one or more diagnoses. The output data, including the probability and/or confidence interval data, may then be sent by a first computing device executing a first application and received by a second computing device executing a second application. The computing device executing an application that receives the output data may also receive an indication that the medical patient with whom the output data is associated with will be seen by a medical service provider at a given time. The output data may then be surfaced and displayed as a notification including the potential diagnosis.

The medical service provider may receive the notification of the potential diagnosis and may make a decision on whether to confirm or reject the diagnosis. This process may occur during a patient encounter, such as a patient visit at the doctor's clinic, or other healthcare setting, or it may occur independent of an in-person medical service provider and patient interaction, such as a telehealth consult, asynchronous medicine, and/or other forms of medical practice. The confirmation or rejection of the diagnosis may lead to updating the data in the patient file as well as the database and provides feedback on the diagnosis. If another diagnosis has been surfaced, it may display after the first diagnosis, after which the process may repeat until there are no more diagnosis left to confirm or reject.

The machine learning models may be configured to diagnose one or more diseases or conditions. The individual machine learning models may trained to determine a likelihood that a disease or condition should be diagnosed in a medical patient, such models may be trained and configured for specific disease groups. For example, the disease groups may comprise: cancer, chronic kidney disease, heart disease, congestive heart failure, vascular disease, morbid obesity, diabetes, etc. The models developed and trained for each disease groups may have overlapping features with other models as well as independent features from other models. The selected features, the normalization, standardization, and transformation of data may be similar across different disease focused models, or they may be orthogonal.

The data used to train and execute the machine learning models may be based on health record data, insurance data, socioeconomic status data, behavioral data, or other forms of data that relate to diagnosis suspecting. In examples, these data may include but are not limited to at least data from medical records, chart codes, Centers for Medicare & Medicaid Services data, International Codes for Diagnosis data, medication data, and laboratory data.

The data may be prioritized and/or weighted for the individual models. Data prioritization and/or weighting may be done based upon predefined criteria, wherein the predefined criteria includes, but is not limited to, at least one of documented International Classification of Disease codes, medication for singular disease, laboratory values that define diagnosis, etc. The prioritization and/or weighting may also be determined through the processes of training the machine learning models. For example, the prioritization and/or weighting may occur by determining an impact of a data type on the output data. The prioritization may also determining the impact satisfies a threshold impact. In other examples data types may be prioritized based upon the effect that data has on the outcome.

The determining of a diagnosis diagnoses of one or more diseases or conditions associated with the medical patient utilizing machine learning includes, determining that a combination of features, which may be known as risk factors, may be associated with one or more diseases or conditions. This association represents a relationships between the risk factors and the diseases or conditions. The determination of whether the association results in a positive diagnosis may be whether the association satisfies a threshold for a confirmation of diagnosis.

When the medical service provider confirms or rejects the diagnosis the decision may be added to the medical patients record, as well as updating the database. This decision which can be coded as a true-positive, false-positive, true-negative, or false-negative may also be fed back into the database. These determinations are then used to retrained and hone the model to improve the sensitivity, specificity, and overall accuracy of the machine learning models.

The machine learning models may be retrained, updated, and honed over time through receiving feedback. This process may occur, for example, by receiving feedback data over a period of time; inputting feedback data into the machine learning models and using this data to retrain the features and their respective weights and variance structures; receiving an indication of criteria; and updating the machine learning models to determine the diagnosis of one or more diseases or conditions based at least in part on the criteria.

Additional details are described below with reference to several example embodiments.

FIG. 1 illustrates a schematic diagram of an example environment 100 for the utilization and implementation of diagnosis suspecting architecture and systems. The environment might include a medical service provider 102 (e.g. physician, nurse practitioner, physician's assistant), a medical patient 104, and a computing device 106 that includes a display 108, one or more processors 110, a network interface (s) 111, and memory 112 that houses one or more applications 114. The computing device 106 may be connected, through a network 116, to one or more remote computing resources 118. The remote computing resource(s) may include a one or more components, such as, for example, a computing device 120 that houses one or more processors 122, input and/or output devices 124, a display device 126, a network interface, and memory 130. The memory may contain one or more of a database 132, a data acquisition component 134, machine learned models, 136, a notification component 138, a data formatting component 140, medical patient profiles 142, and a feature selection component.

The remote computing resource 118 houses the hardware and software that may generate machine learning models configured to diagnose one or more diseases or conditions and may utilized the trained machine learning models 136 to determine a likelihood that a disease or condition should be diagnosed in a medical patient 104 and then surfacing that diagnoses to a medical service provider 102 on a remote device that may be running an application 114 housed in the memory 112 and executed by the processors. This application 114 may be, at least in part, designed to receive the notification of a diagnosis sent by the notification component 138 and show the diagnosis to the medical service provider 102 through the display 108. The machine learned models 136 may be trained on a large data set stored in the database 132, wherein individual machine learning models may be trained to determine a likelihood that a disease or condition should be diagnosed in a medical patient 104.

The data used to train the machine learning models may be received into a database 132 from multiple disparate data sources via a computing network 116. On their own, the data from the disparate sources may exist in disparate formats and may undergo formatting into coherent data structures and formats in the data formatting component 140. These data structures may be multi-dimensional data and may include associated meta-data that may be unpacked and formatted within the data structures. Annotations may be included in the disparate data sources and involve formatting. The data structures may be further formatted into model features that may be configured to be inputs into machine learning models through the use of a feature selection component 144. Formatting data into model features may include several data manipulations. For example, data may be standardized or normalized to bring data with different scales into a similar scale. New data may be generated in appropriate scales using other techniques appropriate for machine learning models.

The formatted data may then be input into the machine learned models 136, wherein the diagnosis suspecting occurs. The diagnosis output data, which may include a probability and a confidence value, may then be sent to the notification component 138. The notification component may send the information through the network 116 to the remote device, which may then surfaces the diagnosis through the application 114 and display the diagnosis to the medical service provider 102. The medical service provider may then confirm or reject the diagnosis. The decision data may then be sent through the network 116 to the remote computing resource(s), routed through the data acquisition component, and stored in the database 132 and medical patient profiles 142.

As used herein, a processor, such as processor(s) 110 and/or 122, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 110 and/or 122 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 110 and/or 122 may possess its own local memory, which also may store program components, program data, and/or one or more operating systems.

The memory 112 and/or 130 may include volatile and nonvolatile memory, removable and non-removable media implemented in any method or technology for storage of information, such as computer-readable instructions, data structures, program component, or other data. Such memory 112 and/or 130 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 112 and/or 130 may be implemented as computer-readable storage media ("CRSM"), which may be any available physical media accessible by the processor(s) 110 and/or 122 to execute instructions stored on the memory 112 and/or 130. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 112 and/or 130, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Wash., USA; the Windows operating system from Microsoft Corporation of Redmond, Wash., USA; LynxOS as promulgated by Lynx Software Technologies, Inc. of San Jose, Calif.; Operating System Embedded (Enea OSE) as promulgated by ENEA AB of Sweden; and so forth.

The network 116 may enable communications between the components and/or devices shown in environment 100 and/or with one or more other remote systems, as well as other networked devices. Such network(s) 116 may include one or more network interface controllers (NICs) or other types of transceiver devices to send and receive communications over the network 108.

For instance, each of the network(s) 116 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network(s) 116 may include a wide area network (WAN) component to enable communication over a wide area network.

Figure 2:
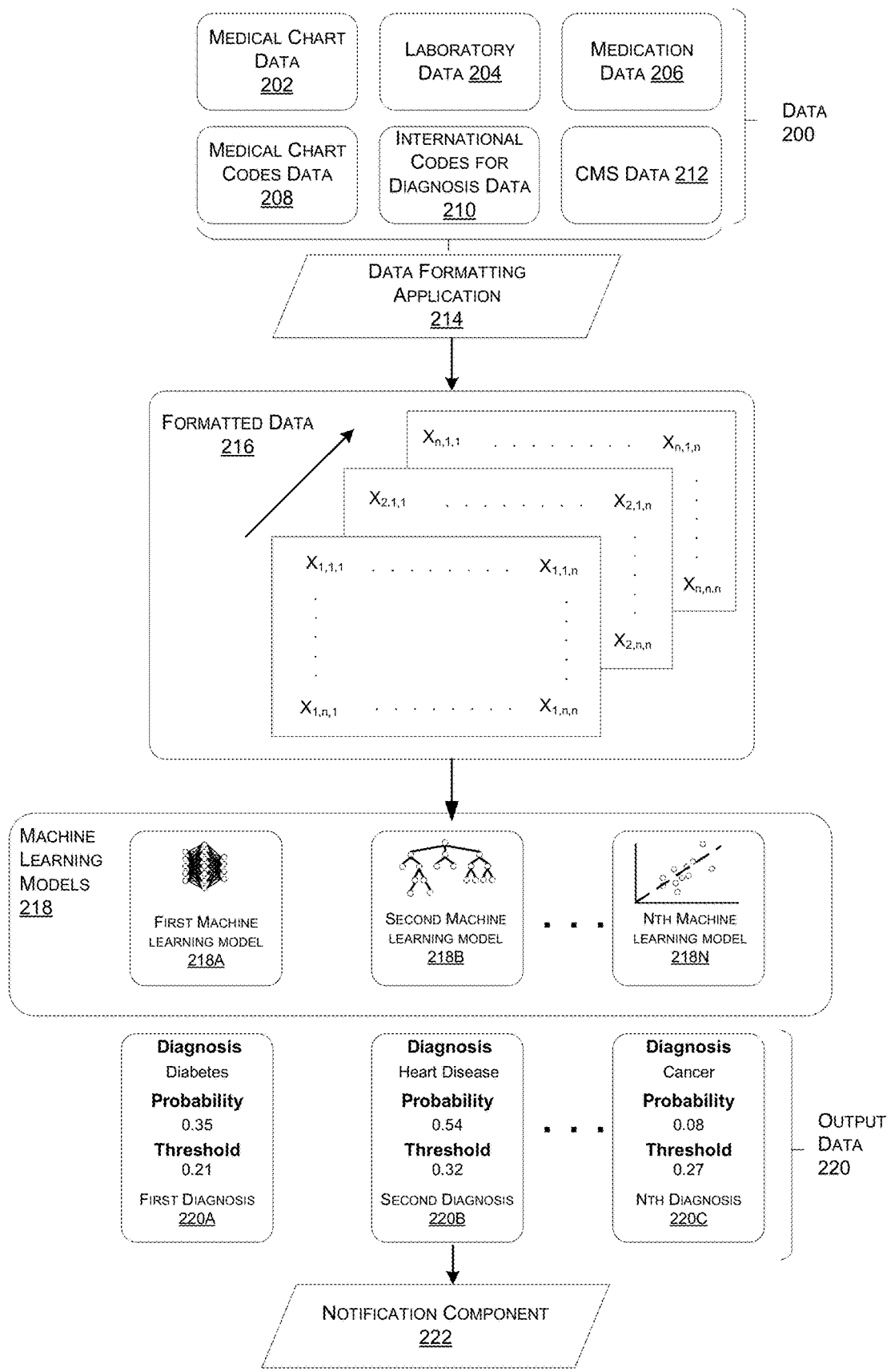
FIG. 2 illustrates a conceptual diagram of example components of diagnosis suspecting architectures and systems.

FIG. 2 illustrates a conceptual diagram of example components of diagnosis suspecting architecture and systems. Data 200 from disparate sources may include at least one of: medical chart data 202, laboratory data 204, medication data 206, medical chart codes 208, international codes for diagnosis data 210, and Centers for Medicare and Medicaid Services (CMS) data 212. These data may then be fed into a data formatting application 214, in which data may be formatted into model features and configured such that it may be inputted into machine learning models. The formatted data 216 may be multidimensional data that occupies N dimensional space and formatted to fit individual machine learning models. The formatted data may be fed into machine learning models 218A-218N (hereinafter referred to individually as "item 218A," "item 218B," etc., and generically as "item 218"), wherein the individual machine learning models may be trained on individual disease groups, and may include at least one of cancer, chronic kidney disease, heart disease, congestive heart failure, vascular disease, morbid obesity, diabetes, etc. The machine learning models may generate output data 220A-220N (herein after referred to individually as "item 220A", "item 220B", etc., and generically as "item 220"). The output data 220 may include data regarding a diagnosis (e.g. diabetes, heart disease, cancer), along with additional data such as probability data and threshold data. The output data may then be sent to the notification component 222 which may transfer the notification from the remote computing resource 118 to the computing device 106 via the network 116 and display the notification to the medical service provider 102.

The medical chart data 202 may include data on at least one of family health history, diet data, exercise, sexual history, smoking, alcohol consumption, immunization records, motor development, cognitive, intellectual, age, sex, race, religion, occupation, surgical history, obstetric history, allergies, hospital admissions, specialist consultations, physical check up visits. Laboratory data 204 may include data on at least one of cell counts (e.g., red blood cell count, hematocrit, neutrophil count, lymphocyte count, monocyte count, eosinophil count, basophil count), cardiac markers (e.g., troponin I, troponin T, myoglobin), general chemistries (e.g., albumin, alkaline phosphatase, anion gap, ammonia, ALT, AST, bilirubin, blood urea nitrogen, creatinine, creatine, calcium, chloride, carbon dioxide, ethanol, folic acid, glucose, HDL, LDL, iron, iron binding capacity, lactic acid, lactate, lipase, magnesium, osmolarity, parathyroid hormone, phosphorous, sodium, T3, T4, TSH, uric acid, triglycerides), urine data (e.g., color, specific gravity, pH, sodium, potassium, protein, amylase, creatinine, magnesium), and coagulation data (e.g., thrombin time, platelets, plasminogen, fibrinogen, bleeding time). While these laboratory data are enumerated, many more are contemplated. Medication data 206 may include data on at least one of medication name, medication class, dosage, refill times, route of administration, drug interactions, and contraindications. Medical chart codes data 208 may include data on at least one of chart codes for tests, surgeries, evaluations, procedures, surgeries, and prescriptions. International codes for diagnosis (ICD) data 210 may include data on at least one of codes for diagnoses, symptoms, and procedures through the ICD coding system.

The data formatting application 214 may receive the data 200 that may be derived from multiple disparate data sources via a computing network 116. On their own, the data from the disparate sources may exist in disparate formats and may be formatted into coherent data structures and formats in the data formatting application 214. These data structures may be multi-dimensional data and may include associated meta-data that may be unpacked and formatted within the data structures. Annotations may be included in the disparate data sources and include formatting. The data structures may be further formatted into model features that may be configured to be inputs into machine learning models. Formatting data into model features may involve several data manipulations. For example, data may be standardized or normalized to bring data with different scales into a similar scale. Data standardization is the process of rescaling the features, such that they may have the properties of a Gaussian distribution where the mean is equal to zero and the standard deviation is equal to one. Data normalization is the process of rescaling the features such that the range of the data is fixed. For example, the range can be fixed between zero and one, and normalized based on a sigmoid function. In other examples, the range can be fixed between zero and 10, and normalized based on a rectified linear unit function. While these standardization and normalization approaches are discussed, many others are contemplated. New data may be generated in appropriate scales using other techniques appropriate for machine learning models.

The data formatting application 214 may output formatted data 216. The formatted data 216 may be multidimensional data and exist in N dimensional space. The data may exist as singular data frames or data sets or as multiple data frames or data sets in one or more different layers as shown in FIG. 2. The formatted data may include meta-data that provides additional annotation for machine learning models or be dynamic data frames that can scale depending on models and applications. The data may exist in a myriad of formats, including, but not limited to, tab delineated formats, rich text formats, comma separated values, excel spreadsheets, XML files, html files, or other readable and/or writable data formats.

The formatted data 216 may be fed into machine learning models 218, wherein the individual machine learning models 218 are trained to disease groups. The different machine learning models may comprise different architectures and/or hyperparameters compared to one another. For example, training a first machine learning model may comprise training one or more machine learning models having different architectures and/or hyperparameters and selecting the first machine learning model from among the machine learning models based at least in part on an accuracy metric, model complexity, and/or processing speed associated with the first ML model.

FIG. 2 depicts several machine learning models that may be used depending on the data structures and the disease groups. 218A depicts a multi-layer perceptron (MLP) having an input layer comprising input node(s), a single hidden layer (intervening the input node(s) and the output node(s), and an output layer comprising output node(s). In some examples, the number of input nodes may equal the number of column vectors present in a data set, and the number of output nodes may be equal to the outcome of a diagnosis (e.g., positive or negative). For example, the multilayer perceptron may be trained to output a diagnosis of diabetes based on input data including laboratory values and medication data. 218B depicts a random forest algorithm that may take an initial data set and walk through decision trees to arrive at a positive or negative diagnosis. 218N depicts a linear regression which may take a multidimensional dataset and utilize linear regression to arrive at a positive or negative diagnosis. In addition to these machine learning algorithms, the machine learning models may also comprise, for example, a support vector machine (SVM) (e.g., Nystroem Kernel SVM, radial basis function (RBF) kernel SVM), a regression algorithm (e.g., ordinary least squares regression (OLSR), linear regression, logistic regression, Ridge regression, Lasso regression, ElasticNet regression), decision tree algorithms (e.g., classification and regression tree (CART), iterative dichotomiser 3 (ID3), Chi-squared automatic interaction detection (CHAID), decision stump, conditional decision trees, LightGBM, gradient-boosting machines (GBM), gradient boosted regression trees (GBRT))), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), a neural network (e.g., a multilayer perceptron (MLP), ResNet50, ResNet101, ResNet 152, VGG, DenseNet, PointNet).

FIG. 2 also depicts output data 220 that may be generated from the machine learning models 218. The output data 220 may include data regarding a diagnosis (e.g., diabetes, cancer, heart disease), as well as a probability and a threshold. Other output data 220 may also be included, such as confidence values for point estimates, sensitivity, specificity, and model fit statistics (e.g., Akaike's information criterion, R values, area under the curve). In an example, 220A depicts output data 220 for a first diagnosis, wherein the diagnosis is diabetes, and a probability of 0.35. In this example, the probability satisfies a threshold of exceeding 0.21, indicating a positive diagnosis. In another example, 220B depicts output data 220 for a second diagnosis, wherein the diagnosis is heart disease, and a probability of 0.54. In this example, the probability satisfies a threshold of exceeding 0.32, indicating a positive diagnosis. In another example, 220N depicts output data 220 for an $N^{th}$ diagnosis, wherein the diagnosis is cancer, and a probability is 0.08. In this example, the probability fails to satisfy a threshold of exceeding 0.27, indicating a negative diagnosis. While in these examples satisfying a threshold involves a probability exceeding a threshold, being less than, equal to, or any other iteration of satisfying a threshold can be utilized.

Figure 3:
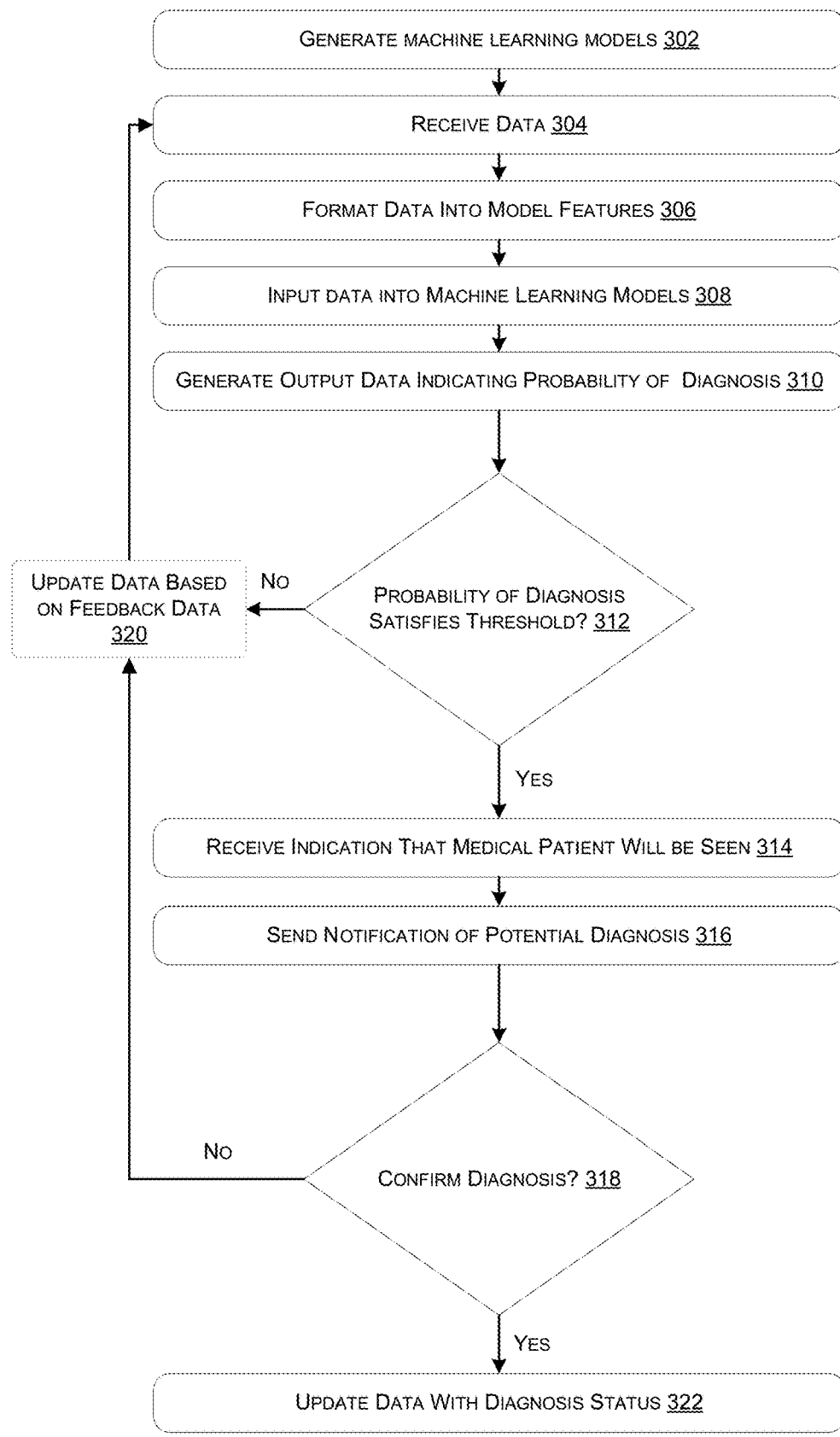
FIG. 3. illustrates a flow diagram of an example process for utilizing machine learning models trained for diagnosis suspecting.

FIG. 3 illustrates a flow diagram of an example process for utilizing machine learning models trained for diagnosis suspecting. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1, 2, and 4-7, although the processes may be implemented in a wide variety of other environments, architectures and systems.

FIG. 3 illustrates a flow diagram of an example process 300 for diagnosis suspecting. The order in which the operations or steps are described is not intended to be construed as a limitation, and any number of the described operations may be combined in any order and/or in parallel to implement process 300.

At block 302, the process 300 may include generating one or more machine learning models. For example, the machine learning models may be configured to diagnose one or more diseases or conditions. The trained machine learning models may then be used to determine a likelihood that a disease or condition should be diagnosed in a medical patient. and then surfacing that diagnoses to a medical service provider.

At block 304, the process 300 may include receiving data 304, wherein the data may consist of data from disparate sources received through a network and deposited into a database. The data used to train the machine learning models may be received into a database from multiple disparate data sources via a computing network. On their own, the data from the disparate sources are likely to exist in disparate formats and may be formatted into coherent data structures and formats. These data structures may be multi-dimensional data and may include associated meta-data that may be unpacked and formatted within the data structures.

At block 306, the process 300 may include formatting data into model features. Annotations may be included in the disparate data sources and include formatting. The data structures may then be further formatted into model features and may be configured to be inputs into machine learning models. Formatting data into model features may involve several data manipulations. For example, data may be standardized or normalized to bring data with different scales into a similar scale. New data may be generated in appropriate scales using other techniques appropriate for machine learning models.

At block 308, the processes 300 may include inputting data into machine learning models 308. The machine learning models may be individually trained to specific diagnoses. The machine learning models may receive the inputted, formatted data and may process the data utilizing machine learning approaches. The machine learning approaches may comprise support vector machine (SVM) (e.g., Nystroem Kernel SVM, radial basis function (RBF) kernel SVM), a regression algorithm (e.g., ordinary least squares regression (OLSR), linear regression, logistic regression, Ridge regression, Lasso regression, ElasticNet regression), decision tree algorithms (e.g., classification and regression tree (CART), iterative dichotomiser 3 (ID3), Chi-squared automatic interaction detection (CHAID), decision stump, conditional decision trees, LightGBM, gradient-boosting machines (GBM), gradient boosted regression trees (GBRT))), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), a neural network (e.g., a multilayer perceptron (MLP), ResNet50, ResNet101, ResNet 152, VGG, DenseNet, PointNet.

At block 310, the processes 300 may include generating output data indicating probability of diagnosis. The output data may include at least a probability and a confidence value that a medical patient should be diagnosed with one or more diagnoses. Other output data may include sensitivity data, specificity data, Akaike's information criterion, area under the curve or other measures of model fit and classification accuracy.

At block 312, the processes 300 may include determining that the probability of diagnosis satisfies a threshold. In examples, satisfying a threshold may include a probability of a diagnosis exceeding a threshold value. In other examples, satisfying a threshold may include a probability of diagnosis falling below a threshold value. In other examples, satisfying a threshold may include a probability of diagnosis being equal to a threshold value. In examples, the probability of diagnosis does not satisfy the threshold and the process may proceed to block 320, wherein the system and methods update data based on feedback data 320. In other examples, the probability of diagnosis satisfies the threshold and the process 300 may proceed to block 314, wherein the systems and methods receive an indication that a medical patient will be seen 314.

At block 314, the process 300 may include receiving an indication that a medical patient will be seen. In examples, the systems and methods may utilize medical charts and medical scheduling data to determine that a patient may be seen in a given time window. Determining that a medical patient may be seen in a given time window may prompt the process to surface the diagnosis in the medical patient's chart and/or user profile.

At block 316, the process 300 may include sending a notification of potential diagnosis. The notification may be sent to a medical service provider during a patient encounter, prior to a patient encounter, or after a patient encounter. The notification may alert the medical service provider and then surface the diagnosis to the medical service provider.

At block 318, the process 300 may include a decision to confirm the diagnosis. medical service provider. If the confirmation of the diagnosis is rejected, the system and methods update data based on feedback data that the medical service provider rejected the diagnosis. If the medical service provider positively confirms the diagnosis, then the system and methods update data with diagnosis status.

At block 320, the process 300 may include updating data based on feedback data. In examples the feedback data may be received from block 312, wherein the probability of diagnosis may not satisfy the threshold. These feedback data may be fed back into the model to update and improve the model. In other examples, the feedback data may be received from block 318, wherein a diagnosis may not by confirmed by a medical service provider.

Figure 4:
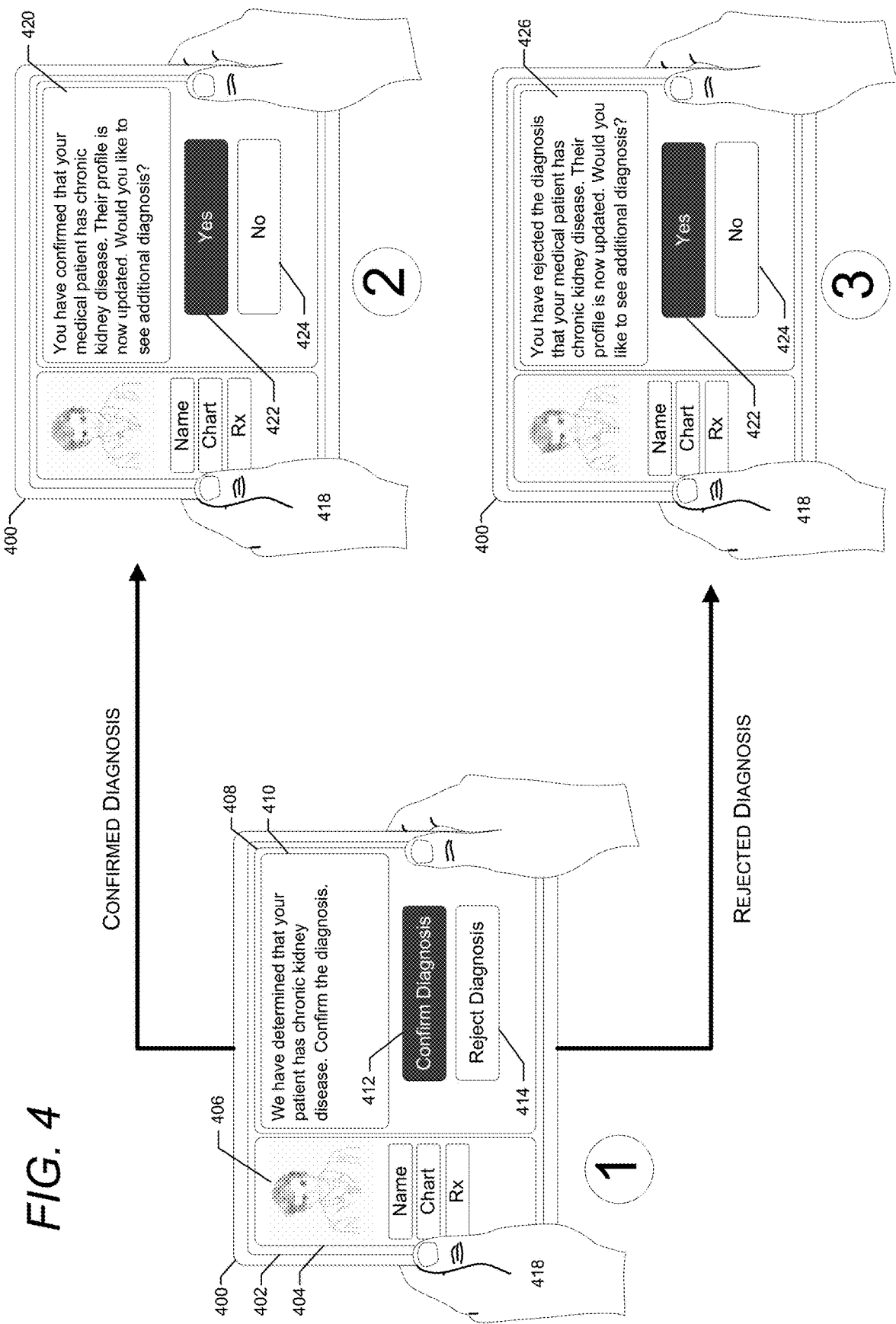
FIG. 4 illustrates an example user interfaces utilized for confirming or rejecting a diagnoses surfaced from diagnosis suspecting utilizing the machine learning models described herein.

FIG. 4 illustrates example user interfaces utilized for confirming or rejecting a diagnoses surfaced from diagnosis suspecting utilizing the machine learning models described herein. The decision tree bifurcation shown in FIG. 4 is illustrated by arrows. The device 400, which may be a computing device, may include a display 402 having a first area 404 and a second area 408. For instance, the first area 404 may include an image of a patient 406 along with the name, medical chart, and prescription information. However, while FIG. 4 illustrates certain background information, other information may be displayed as well, or the background information may be presented differently than shown. The background information may be accessed through a user 418 interacting with the display 402. For instance, the user 418 may select "Chart" within the first area and medical charts of the patient may be displayed on the display 402.

Shown at "1," the second area 408 may display a first prompt within a first field 410 that relates to a diagnosis. This diagnosis has been received from the notification component 138 and 222. The user 418 may respond to the first prompt by selecting a button to confirm diagnosis 412 or by selecting a button to reject diagnosis 414. Shown at "2", if the diagnosis is confirmed, then the device 400 may proceed to populate the second area 408 with a new prompt 420, notifying the user 418 that the diagnosis was confirmed and the profile was updated, and may ask the user 418 if they would like to see additional diagnosis. The user 418 may select to proceed to an additional diagnosis by selecting the yes button 422 or end the process by selecting the no button 424. Shown at "3" if the initial diagnosis is rejected, then the device 400 may proceed to populate a different second area 426 with a new prompt 426, notifying the user 418 that the diagnosis was rejected and the profile was updated, and may ask the user 418 if they would like to see additional diagnosis. The user 418 may select to proceed to an additional diagnosis by selecting the yes button 422 or may end the process by selecting the no button 424.

Figure 5:
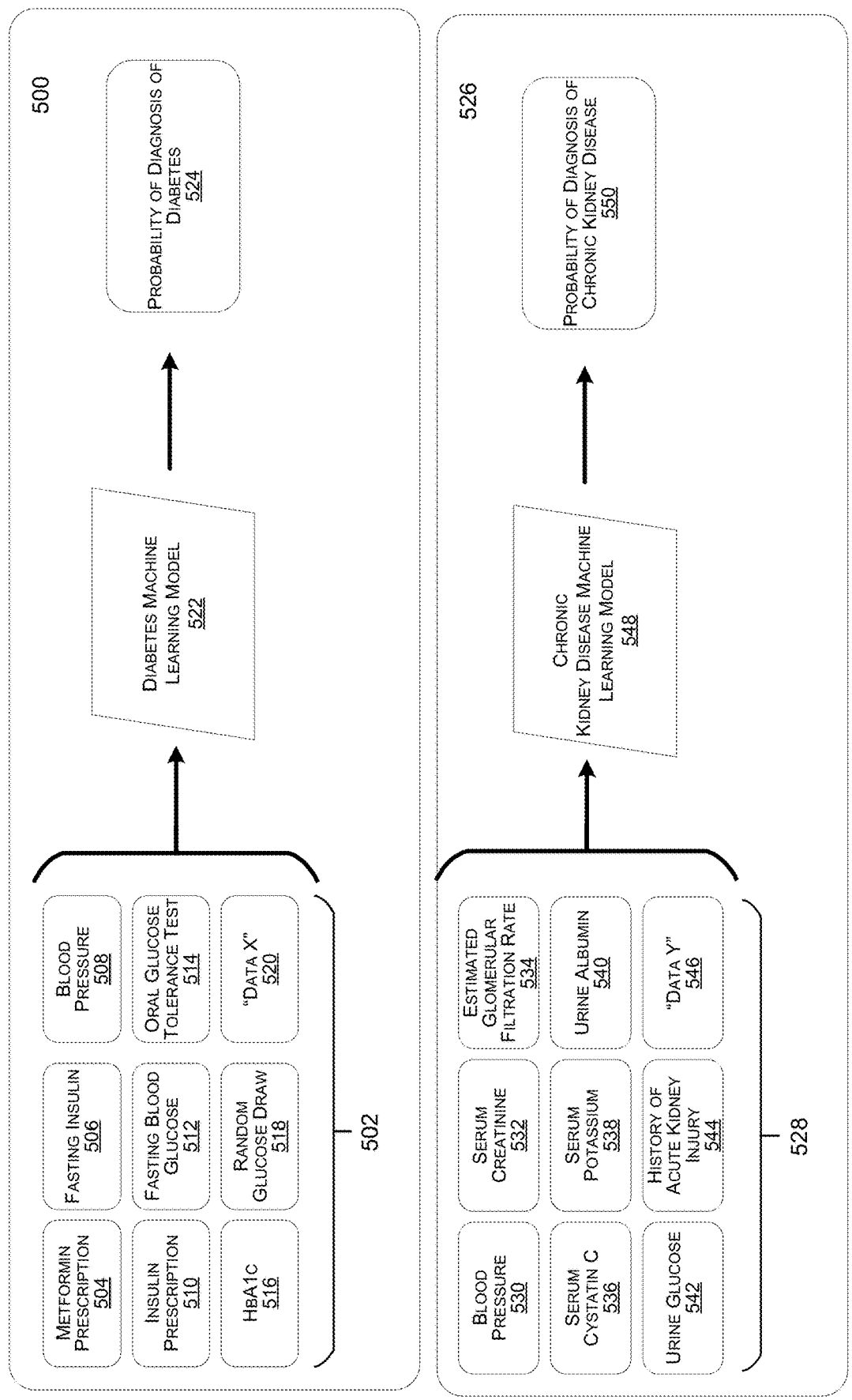
FIG. 5 illustrates a conceptual diagram of components of input data, machine learning models, and output data associated with diagnosis suspecting.

FIG. 5 illustrates a conceptual diagram of components of input data, machine learning models, and output data associated with diagnosis suspecting. Environment 500 describes the process and space in which a machine learning model 522 may receive input data 502 and may generate a probability of diagnosis of diabetes 524. The input data may be prioritized for the diabetes machine learning model 522 through a priori knowledge or prioritization strategies based on predefined criteria or through machine learning techniques to harvest data. A priori knowledge or prioritization may be based on clinical knowledge. In an example, a metformin prescription 504 may provide prognostic information toward a diagnosis of diabetes as metformin can be used to manage diabetes; however, metformin may also be used for other metabolic conditions such as polycystic ovarian syndrome and may be used as a part of other data to determine a diagnosis. Other data that may be determine a priori by predefined criteria may include but is not limited to fasting insulin 506, blood pressure 508, insulin prescription 510, fasting blood glucose 512, oral glucose tolerance test 514, glycated hemoglobin (HbA1c) 516, or a random glucose draw 518. In other examples, data may be selected based on machine learning techniques. In examples, machine learning techniques may identify "data X" 520 as an important feature for determining a diagnosis, wherein "data X" may be familial history of diabetes, genetic data, BMI data, or other data. In another example, environment 526 describes the process and space in which a machine learning model 548 may receive input data 528 and may generate a probability of diagnosis of chronic kidney disease 550. The input data may be prioritized for the chronic kidney disease machine learning model 548 through a priori knowledge or prioritization strategies based on predefined criteria or through machine learning techniques to harvest data. A priori knowledge or prioritization may be based on clinical knowledge. In an example, a blood pressure 530 may provide prognostic information toward a diagnosis of chronic kidney disease as dysregulated blood pressure can be a symptom of chronic kidney disease; however, blood pressure may also be indicative of a different disease process (e.g. primary hypertension) and may be used as a part of other data to determine a diagnosis. Other data that may be determine a priori by predefined criteria may include but is not limited to serum creatinine 532, estimated glomerular filtration rate 534, serum cystatin C 536, serum potassium 538, urine albumin 540, urine glucose 542, and history of acute kidney injury 544. Data may also be selected based on machine learning techniques. In examples, machine learning techniques may identify "data y" 546 as an important feature for determining a diagnosis, wherein "data y" may be SNP in the APOL1 gene or presence of diabetes.

Figure 6:
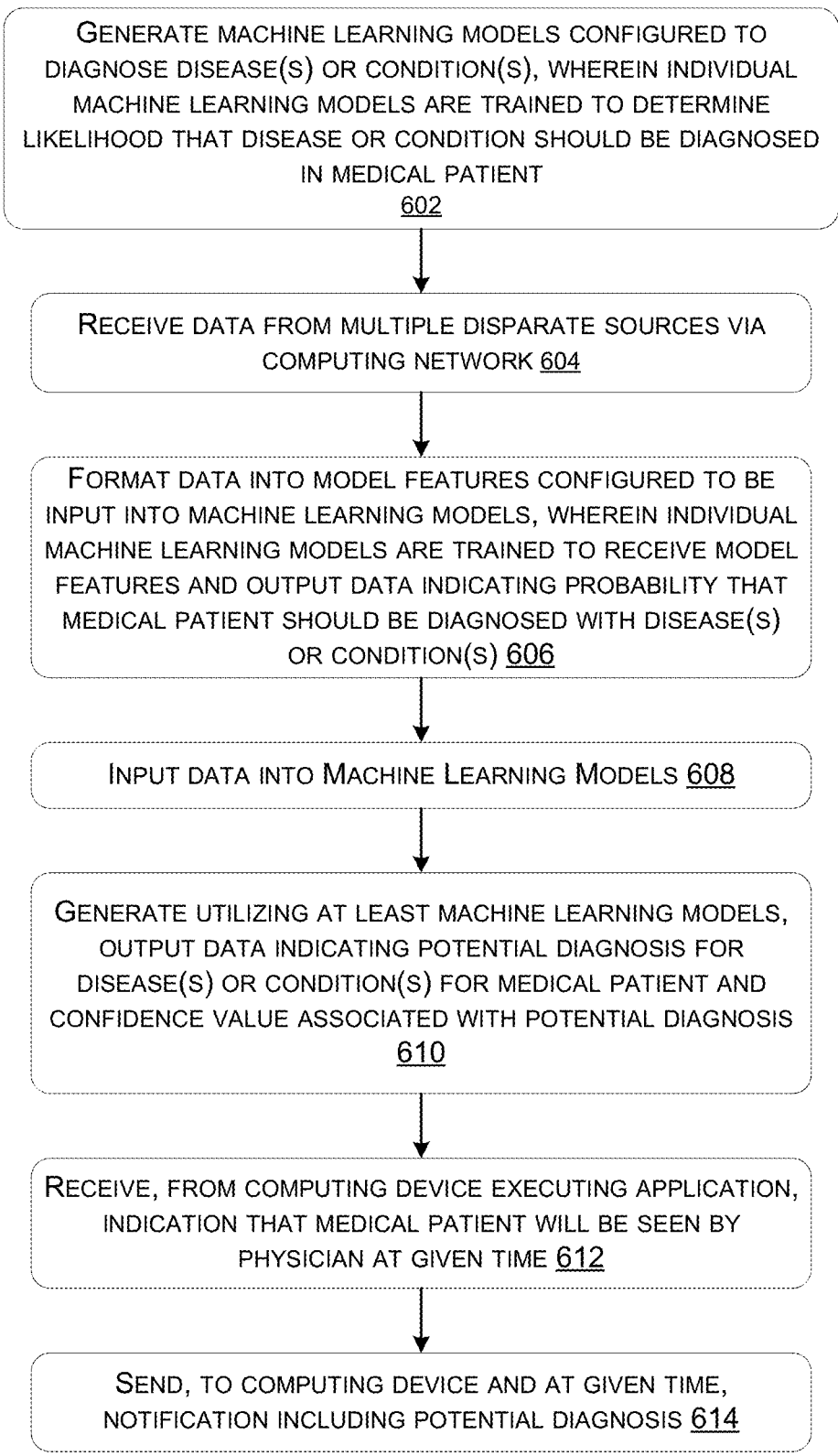
FIG. 6 illustrates a flow diagram of an example process for utilizing machine learning models for diagnosis suspecting.

FIG. 6 illustrates a flow diagram of an example process for utilizing machine learning models for diagnosis suspecting. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-5 and 7, although the processes may be implemented in a wide variety of other environments, architectures and systems.

FIG. 6 illustrates a flow diagram of an example process 600 for diagnosis suspecting. The order in which the operations or steps are described is not intended to be construed as a limitation, and any number of the described operations may be combined in any order and/or in parallel to implement process 600.

At block 602, the process 600 may include systems and methods that may generate machine learning models configured to diagnose disease(s) or condition(s), wherein individual machine learning models may be trained to determine a likelihood that disease or condition should be diagnosed in medical patient.

At block 604, the process 600 may include receiving data from multiple disparate sources via computing network. On their own, the data from the disparate sources are likely to exist in disparate formats and may be formatted into coherent data structures and formats. These data structures may be multi-dimensional data and may include associated metadata that may be unpacked and formatted within the data structures.

At block 606, the process may include, generating new data with a format in which the data is structured into model features configured to be input into machine learning models, wherein individual machine learning models are trained to receive model features and output data indicating probability that medical patient should be diagnosed with disease(s) or condition(s). The data from the disparate sources may exist in variable and distinct formats and may include formatting into coherent data structures and formats in the data formatting component. These data structures may be multi-dimensional data and may include associated metadata that may be unpacked and formatted within the data structures. Annotations may be included in the disparate data sources and include formatting. The data structures may be further formatted into model features that are configured to be inputs into machine learning models through the use of a feature selection component. Formatting data into model features may involve several data manipulations. For example, data may be standardized or normalized to bring data with different scales into a similar scale. New data may be generated in appropriate scales using other techniques appropriate for machine learning models.

At block 608, the process 600 may include inputting data that is input into machine learning models. Inputting data into the machine learning models may include uploading data into a data frame on a server or a local machine, into a computational environment that allows for programming and executing machine learning models (e.g. The R Project for Statistical Computing, Python, PyTorch, AWS, TensorFlow, Shogun, Keras, Apache, Oryx, RapidMiner, KNIME).

At block 610, the process 600 may include generating, utilizing at least machine learning models, output data indicating potential diagnosis for disease(s) or condition(s) for medical patient and confidence value associated with potential diagnosis. In an example, the machine learning models may be configured to diagnose one or more diseases or conditions, wherein individual machine learning models may be trained to determine a likelihood that a disease or condition should be diagnosed in a medical patient may be trained and configured for specific disease groups. For example, the disease groups may comprise: cancer, chronic kidney disease, heart disease, congestive heart failure, vascular disease, morbid obesity, diabetes, etc. The models developed and trained for each disease groups may have overlapping features with other models as well as independent features from other models. The selected features, the normalization, standardization, and transformation of data may be similar across different disease focused models, or they may be entirely independent data vectors. In an example, the machine learning models may determine a diagnosis, based at least in part on machine learning techniques, that a combination of risk factors, which may be derived at least in part from the data, is associated with one or more diseases or conditions, and the association may exceed a threshold for a confirmation of diagnosis the output data includes a probability and confidence value that a medical patient should be diagnosed with one or more diagnoses. The output data, including the probability and confidence interval data, may then sent by a computing device executing an application and received by another computing device executing an application.

At block 612, the process 600 may include the computing device executing an application that may receive the output data, and then may receive an indication that the medical patient with whom the output data is associated with will be seen by a medical service provider at a given time. The output data may then be surfaced and displayed as a notification including the potential diagnosis.

At block 614, the process 600 may include sending the notification to the computing device at a given time, generally during an encounter between the medical service provider and the patient, and then surfacing the diagnosis on a device, wherein the medical service provider may review the patients chart, medical history, and other salient information and then may confirm or reject the diagnosis.

The process 600 may include user data that relates at least, but is not limited to the health, socioeconomic status, geographic location, genetic history, and behaviors of the user. The data may include, but is not limited to medical records, chart codes, Centers for Medicare & Medicaid Services data, International Codes for Diagnosis data, medication data, and laboratory data.

The process 600 may also include diagnosis of one or more diseases or conditions associated with the medical patient. These diagnoses may involve determining, based at least in part on machine learning techniques, that a combination of risk factors, which are derived at least is associated with one or more diseases or conditions. These risk facts may be derived, at least in part from the data. In examples, the diagnoses may include criteria that the association with one or more diseases or conditions satisfies a threshold for a confirmation of diagnosis.

The process 600 may be based at least in part on machine learning techniques, wherein the machine learning techniques may utilize models that have been trained on disease groups. These disease groups may include, but are not limited to cancer, chronic kidney disease, heart disease, congestive heart failure, vascular disease, morbid obesity, diabetes, etc.

The process 600 may include feedback data being incorporated into the machine learning techniques. The feedback may include indications of whether the surfaced diagnosis was correct and being used to hone the model. The feedback may also be used to adjust probabilities and thresholds of the models. The feedback may be received over a period of time and fed into the machine learning models at regular intervals, irregular intervals, or continuously. The machine learning models may be updated based on the feedback data at regular intervals, irregular intervals, or continuously.

The process 600, may involve prioritizing data prior to training the machine learning models. The prioritization may be based upon predefined criteria. These predefined criteria may include, but are not limited to International Classification of Disease codes, medication data, and laboratory data. The prioritization may also be based on machine learning approaches and weights determined by the machine learning techniques. This type of prioritization may include determining the impact specific data type may have on output data, determining that the impact satisfies a threshold impact, and may then prioritize the data type.

FIG. 7 illustrates a flow diagram of another example process for utilizing machine learning models for diagnosis suspecting. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-6, although the processes may be implemented in a wide variety of other environments, architectures and systems.

FIG. 7 illustrates a flow diagram of another example process 700 for utilizing machine learning models for diagnosis suspecting. The order in which the operations or steps are described is not intended to be construed as a limitation, and any number of the described operations may be combined in any order and/or in parallel to implement process 600.

At block 702, the process 700 may include systems and methods that may generate machine learning models configured to diagnose disease(s) or condition(s) for a medical patient. This may occur at least in part through a process by which the system may receive, at block 704, data from multiple disparate sources via computing network. The data from disparate sources may include medical chart data, laboratory data, medication data, medical chart codes data, international codes for diagnosis data, and CMS data.

At block 706, the process 700 may include taking the data that has been received and the systems and methods and may format data into model features configured to be input into machine learning models. The data from the disparate sources may exist in variable and distinct formats and may include formatting into coherent data structures and formats in the data formatting component. These data structures may be multi-dimensional data and may include associated metadata that may be unpacked and formatted within the data structures. Annotations may be included in the disparate data sources and include formatting. The data structures may be further formatted into model features that are configured to be inputs into machine learning models through the use of a feature selection component. Formatting data into model features may involve several data manipulations. For example, data may be standardized or normalized to bring data with different scales into a similar scale. New data may be generated in appropriate scales using other techniques appropriate for machine learning models.

At block 708, the process 700 may include inputted the formatted model features into machine learning models. Inputting data into the machine learning models may include uploading data into a data frame on a server or a local machine, into a computational environment that allows for programming and executing machine learning models (e.g. The R Project for Statistical Computing, Python, PyTorch, AWS, TensorFlow, Shogun, Keras, Apache, Oryx, Rapid-Miner, KNIME).

At block 710, the process 700 may include utilizing the inputted data and model features the process and may then generate, utilizing at least machine learning models, output data indicating potential diagnosis for disease(s) or condition(s) for medical patient. The machine learning models may be configured to diagnose one or more diseases or conditions and the individual machine learning models may be trained to determine a likelihood that a disease or condition should be diagnosed in a medical patient. These models may be trained and configured for specific disease groups. For example, the disease groups may comprise: cancer, chronic kidney disease, heart disease, congestive heart failure, vascular disease, morbid obesity, diabetes, etc. The models developed and trained for each disease groups may have overlapping features with other models as well as independent features from other models. The selected features, the normalization, standardization, and transformation of data may be similar across different disease focused models, or they may be entirely independent data vectors. In this example, the machine learning models may determine a diagnosis, based at least in part on machine learning techniques, that a combination of risk factors, which are derived at least in part from the data, may be associated with one or more diseases or conditions. Determining the diagnosis may be based on the association satisfying a threshold for a confirmation of diagnosis. This may be based on output data that may include a probability and confidence value that a medical patient should be diagnosed with one or more diagnoses. The output data, which may include the probability and confidence interval data, may then be sent by a computing device executing an application and received by another computing device executing an application.

At block 712, the process 700 may include computing device that may execute an application that may receive the output data, and may receive an indication that the medical patient with whom the output data is associated with will be seen by a medical service provider at a given time. The output data may then be surfaced and displayed as a notification including the potential diagnosis.

At block 714, the process 700 may include sending a notification to the computing device at a given time, generally during an encounter between the medical service provider and the patient. The notification may surface the diagnosis on a device 106 or 400, wherein the medical service provider may review the patient's chart, medical history, and other salient information and confirm or reject the diagnosis.

The process 700 may include user data that relates at least, but is not limited to the health, socioeconomic status, geographic location, genetic history, and behaviors of the user. The data may include, but is not limited to medical records, chart codes, Centers for Medicare & Medicaid Services data, International Codes for Diagnosis data, medication data, and laboratory data.

The process 700 may also include diagnoses of one or more diseases or conditions associated with the medical patient. These diagnoses may involve determining, based at least in part on machine learning techniques, that a combination of risk factors, which are derived at least is associated with one or more diseases or conditions. These risk facts may be derived, at least in part from the data. In examples, the diagnoses may include criteria that the association with one or more diseases or conditions satisfies a threshold for a confirmation of diagnosis.

The process 700 may be based at least in part on machine learning techniques, wherein the machine learning techniques may utilize models that have been trained on disease groups. These disease groups may include, but are not limited to cancer, chronic kidney disease, heart disease, congestive heart failure, vascular disease, morbid obesity, diabetes, etc.

The process 700 may include feedback data being incorporated into the machine learning techniques. The feedback may include indications of whether the surfaced diagnosis was correct and being used to hone the model. The feedback may also be used to adjust probabilities and thresholds of the models. The feedback may be received over a period of time and fed into the machine learning models at regular intervals, irregular intervals, or continuously. The machine learning models may be updated based on the feedback data at regular intervals, irregular intervals, or continuously.

The process 700, may involve prioritizing data prior to training the machine learning models. The prioritization may be based upon predefined criteria. These predefined criteria may include but are not limited to International Classification of Disease codes, medication data, and laboratory data. The prioritization may also be based on machine learning approaches and weights determined by the machine learning techniques. This type of prioritization may include determining the impact specific data type may have on output data, determining that the impact satisfies a threshold impact, and may then prioritize the data type.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims.

What is claimed is:

1. A system comprising:
   one or more processors; and
   non-transitory computer-readable media storing first computer-executable instructions that, when executed by the one or more processors, cause the one or more processors to perform operations comprising:
      generating machine learning models configured to diagnose one or more diseases or conditions, wherein individual ones of machine learning models are trained to determine a likelihood that a disease or condition should be diagnosed for a medical patient;
      receiving data from multiple disparate sources via a computing network;
      formatting the data into model features configured to be input into the machine learning models, wherein the individual ones of the machine learning models are trained to receive the model features and output data indicating a probability that the medical patient should be diagnosed with the one or more diseases or conditions;
      inputting the model features into the machine learning models;
      generating, utilizing at least the machine learning models, output data indicating a potential diagnosis associated with the one or more diseases or conditions for the medical patient and a confidence value associated with that potential diagnosis;
      receiving, from a computing device executing an application, an indication that the medical patient will be seen by a medical service provider at a given time;
      receiving an indication that the medical patient is located at a location associated with the medical service provider at the given time; and
      sending, to the computing device and based at least in part on receiving the indication that the medical patient is located at the location associated with the medical service provider at the given time, a command configured to cause a device associated with the medical service provider to display a notification including the potential diagnosis.

2. The system of claim 1, wherein the data includes at least medical records, chart codes, Centers for Medicare & Medicaid Services data, International Codes for Diagnosis data, medication data, and laboratory data.

3. The system of claim 1, the operations further comprising:
   determining, based at least in part on machine learning techniques, that a combination of risk factors, which are derived at least in part from the data, is associated with one or more diseases or conditions; and
   the association exceeds a threshold for a confirmation of diagnosis.

4. The system of claim 1, wherein the machine learning models include individual machine learning models for at least one of cancer, chronic kidney disease, heart disease, congestive heart failure, vascular disease, morbid obesity, or diabetes.

5. A method comprising:
   generating machine learning models configured to diagnose one or more diseases or conditions for a medical patient;
   receiving data from multiple disparate sources via a computing network;
   formatting the data into model features configured to be input into machine learning models;
   inputting the model features into the machine learning models;
   generating, utilizing at least the machine learning models, output data indicating a potential diagnosis for the medical patient;
   assigning a confidence value to the output data indicating a diagnosis for the medical patient;
   receiving, from a computing device executing an application, an indication that the medical patient will be seen by a medical service provider at a given time;
   receiving an indication that the medical patient is located at a location associated with the medical service provider at the given time; and
   sending, to the computing device and based at least in part on receiving the indication that the medical patient is located at the location associated with the medical service provider at the given time, a command configured to cause a device associated with the medical service provider to display a notification including the potential diagnosis.

6. The method of claim 5, wherein the user data includes at least medical records, chart codes, Centers for Medicare & Medicaid Services data, International Codes for Diagnosis data, medication data, and laboratory data.

7. The method of claim 5, wherein the diagnoses of one or more diseases or conditions associated with the medical patient comprises:
   determining, based at least in part on machine learning techniques, that a combination of risk factors, which are derived at least in part from the data, is associated with one or more diseases or conditions; and
   the association exceeds a threshold for a confirmation of diagnosis.

8. The method of claim 5, wherein the machine learning techniques are based, at least in part, on models trained and by disease groups, wherein the disease groups are at least one of cancer, chronic kidney disease, heart disease, congestive heart failure, vascular disease, morbid obesity, or diabetes.

9. The method of claim 5, wherein feedback indicating the diagnosis was correct is inputted by a second user, wherein the feedback data is used to hone the model.

10. The method of claim 5, further comprising:
prioritizing the user data prior to training the machine learning models, based upon predefined criteria, wherein the predefined criteria includes, but is not limited to, at least one of documented International Classification of Disease codes, medication for singular disease, or laboratory values that define diagnosis.

11. The method of claim 5, further comprising:
determining an impact of a data type on the output data;
determining that the impact satisfies a threshold impact; and
prioritizing the data type.

12. The method of claim 5, further comprising:
receiving feedback data over a period of time;
inputting feedback data into the machine learning models;
receiving an indication of criteria; and
updating the machine learning models to determine the diagnosis of one or more diseases or conditions based at least in part on the criteria.

13. A system comprising:
one or more processors; and
non-transitory computer-readable media storing instructions that, when executed by the one or more processors, cause the one or more processors to perform operations comprising:
generating machine learning models configured to diagnose one or more diseases or conditions for a medical patient;
receiving data from multiple disparate sources via a computing network;
formatting the data into model features configured to be input into machine learning models;
inputting the model features into the machine learning models;
generating, utilizing at least the machine learning models, output data indicating a potential diagnosis for the medical patient;
assigning a confidence value to the output data indicating a diagnosis for the medical patient;
receiving, from a computing device executing an application, an indication that the medical patient will be seen by a medical service provider at a given time;
receiving an indication that the medical patient is located at a location associated with the medical service provider at the given time; and
sending, to the computing device and based at least in part on receiving the indication that the medical patient is located at the location associated with the medical service provider at the given time, a command configured to cause a device associated with the medical service provider to display a notification including the potential diagnosis.

14. The system of claim 13, wherein the user data includes at least medical records, chart codes, Centers for Medicare & Medicaid Services data, International Codes for Diagnosis data, medication data, and laboratory data.

15. The system of claim 13, wherein the diagnoses of one or more diseases or conditions associated with the medical patient comprises:
determining, based at least in part on machine learning techniques, that a combination of risk factors, which are derived at least in part from the data, is associated with one or more diseases or conditions; and
the association exceeds a threshold for a confirmation of diagnosis.

16. The system of claim 13, wherein the machine learning techniques are based, at least in part, on models trained and by disease groups, wherein the disease groups are at least one of cancer, chronic kidney disease, heart disease, congestive heart failure, vascular disease, morbid obesity, or diabetes.

17. The system of claim 13, wherein feedback indicating the diagnosis was correct is inputted by a second user, wherein the feedback data is used to hone the model.

18. The system of claim 13, further comprising:
prioritizing the user data prior to training the machine learning models, based upon predefined criteria, wherein the predefined criteria includes, but is not limited to, at least one of documented International Classification of Disease codes, medication for singular disease, or laboratory values that define diagnosis.

19. The system of claim 13, further comprising:
determining an impact of a data type on the output data;
determining that the impact satisfies a threshold impact; and
prioritizing the data type.

20. The system of claim 13, further comprising:
receiving feedback data over a period of time;
inputting feedback data into the machine learning models;
receiving an indication of criteria; and
updating the machine learning models to determine the diagnosis of one or more diseases or conditions based at least in part on the criteria.

* * * * *